United States Patent [19]

Kiyoshige et al.

[11] Patent Number: 4,689,221

[45] Date of Patent: Aug. 25, 1987

[54] ORAL COMPOSITION CONTAINING ANTIBODIES TO *BACTEROIDES GINGIVALIS*

[75] Inventors: Tatsuo Kiyoshige, Hadano; Yasuo Kikuchi, Funabashi; Ichiro Takazoe, Tokyo; Katsuji Okuda, Chiba, all of Japan

[73] Assignee: Lion Corporation, Tokyo, Japan

[21] Appl. No.: 686,904

[22] Filed: Dec. 27, 1984

[30] Foreign Application Priority Data

Dec. 28, 1982 [JP] Japan ................. 58-247930

[51] Int. Cl.$^4$ ............ A61K 39/395; A61K 39/02; A61K 7/26
[52] U.S. Cl. .................. 424/87; 424/85; 424/88; 424/92; 424/49; 424/50; 424/48; 514/900; 514/901; 514/902; 435/253; 435/822; 530/387
[58] Field of Search ........... 424/85, 87, 92, 88, 424/48-50; 260/112 R, 112 B; 435/253, 822; 514/900-902

[56] References Cited

U.S. PATENT DOCUMENTS

| 4,029,760 | 6/1977 | Haltzhauer et al. | 514/902 |
|---|---|---|---|
| 4,243,655 | 1/1981 | Gunther | 424/49 |
| 4,324,782 | 4/1982 | Beck | 514/83 J |
| 4,454,109 | 6/1984 | Hillman . | |
| 4,458,014 | 7/1984 | Ebersale | 435/180 |
| 4,472,373 | 9/1984 | Ryon | 514/902 |
| 4,512,968 | 4/1985 | Komyama et al. | 424/49 |

FOREIGN PATENT DOCUMENTS

| 0128338 | 7/1984 | Japan . |
|---|---|---|
| 0075500 | 4/1985 | Japan . |
| 0075284 | 4/1985 | Japan . |

OTHER PUBLICATIONS

Abstracts–Purification & Characterization of . . . Bacteroides gingivalis, Yoshimura et al, *J Bacteriol* 160(3) pp. 949–957, 1984.
Abstract–Serum Antibodies to Oral Bacteroides Asaccharolyticus . . . Periondonal Disease, Mouton et al, *Infect Imm* 31(1) pp. 182–192, 1981.

*Primary Examiner*—Harold D. Anderson
*Assistant Examiner*—Garnette D. Draper
*Attorney, Agent, or Firm*—Birch, Stewart, Kolasch & Birch

[57] ABSTRACT

An oral composition which prevents periodontal disease such as gingivitis, periodontitis and alveolar pyorrhoea through the prevention of the colonization of *Bacteroides gingivalis* comprises an antibody obtained by immunizing a mammal with an antigen selected from *Bacteroides gingivalis*, its pilus and capsule fractions.

31 Claims, No Drawings

ORAL COMPOSITION CONTAINING ANTIBODIES TO *BACTEROIDES GINGIVALIS*

BACKGROUND OF THE INVENTION

This invention relates to an oral composition which can prevent periodontal disease through suppression of the intraoral colonization of *Bacteroides gingivalis* which is one of the causative bacteria of periodontal diseases.

There are many people having periodontal disease such as gingivitis and periodontitis. The rate of such disease in adults is especially on the increase. Prevention of periodontal diseases will be an important problem in the future circumstance because of an ever increasing number of aged persons.

Periodontal disease is primarily caused by bacteria existing in accumulated plaque in periodontal pockets. A healthy periodontal pocket is usually composed of an overwhelming amount of gram positive bacteria, while the amount of gram negative bacteria increases with the progress of the periodontal disease. *Bacteroides gingivalis, Fusobacterium nucleatum, Eikenella corrodens, Actionabacillus actinomycetemcomitans* and so forth are primarily listed as such gram negative bacteria. In the focal regions of adult patients with severe periodontal disease, gram negative bacteria are detected in most cases among which *Bacteroides gingivalis* is separated in a specially high frequency. In many of these cases, the titer of anti-*Bacteroides gingivalis* antibody in the serum of the patient also increases. In addition, it has been demonstrated that the inoculation of an animal with *Bacteroides gingivalis* aggravates periodontal inflammation. These results indicate that *Bacteroides gingivalis* plays an important role in the development of periodontal diseases.

*Bacteroides gingivalis* adheres to periodontal mucosa by means of its pili and capsule existing on the surface of its bacterial body, thereby proliferating and badly influencing the periodontal region. For the prevention of periodontal diseases, the inhibition of the colonization or suppression of the proliferation of *Bacteroides gingivalis* in the mouth is effective and bactericides are mainly used now for this purpose. In some more specific methods, the inhibition of the colonization of *Bacteroides gingivalis* in the mouth is attempted by using a vaccine. However, since the bacterial body is used as an active vaccine which is directly injected into the living human body in all of these methods, they have problems in terms of both effect and toxicity.

SUMMARY OF THE INVENTION

An object of the present invention is to provide an oral composition having an excellent effect on preventing periodontal disease.

For the purpose of attaining the above object, the present inventors researched a highly safe method of securing the prevention of periodontal disease through effective suppression of the colonization of *Bacteroides gingivalis* in the mouth. As a result, the inventors have found that serum antibody or milk antibody obtained by immunizing mammals with *Bacteroides gingivalis*, its pilus or capsule fraction as an antigen remarkably suppresses the colonization of *Bacteroides gingivalis* in the mouth, and that periodontal diseases can be effectively prevented by blending the above antibody to an oral composition, thereby achieving the object of this invention.

Therefore, the present invention provides an oral composition comprising an antibody obtained by immunizing a mammal with at least one antigen selected from the group consisting of *Bacteroides gingivalis*, its pilus and capsule fractions.

According to this invention, since the oral composition contains the above-mentioned antibody, the colonization of *Bacteroides gingivalis* in the mouth is effectively prevented, resulting in the prevention of periodontal disease such as periodontitis.

In addition, since said antibody is highly safe, the oral composition according to this invention can be safely used.

The above and other objects, features, and advantages of this invention will be more fully understood by reading the following description.

DETAILED DESCRIPTION OF THE INVENTION

An oral composition according to this invention contains an antibody obtained by immunizing mammals with *Bacteroides gingivalis*, its pilus or capsule fraction as an antigen.

As *Bacteroides gingivalis* used in preparing the above antigens, the bacterial strain supplied by the Forsyth Dental Center in Boston, bacterial strains separated from the focal regions of periodontitis, and the like may be used.

*Bacteroides gingivalis* used as an antigen may be prepared according to the well known method, for example, by culturing the bacterium in a medium prepared by adding hemin and menadione to Todd-Hewitt broth before the grown bacterium is washed and treated with formalin. Pili and capsules of *Bacteroides gingivalis* used as antigens may be severed and separated from the bacteria (*Bacteroides gingivalis*) according to the well known method.

The usual method may be adopted in immunizing mammals with said antigens. As mammals to be immunized, rabbits, goats, sheep, horses, cows, etc. may be used.

The antibody (immunoglobulin fractions in the antiserum and the milk) may be separated from the antiserum and the milk according to the ordinary antibody purification method including the salting-out method, the gel-filtration method, ion-exchange chromatography, affinity chromatography, and the like, the salting-out method using ammonium sulfate being preferred. In the salting-out method, the antiserum or the milk is saturated with ammonium sulfate to produce the precipitates, followed by dialyzing the precipitates against physiological saline to obtain the purified precipitates as the antibody. The preferred antibody is obtained from the equine antiserum and the bovine antiserum and milk.

In this invention, the antibody contained in the antiserum and milk obtained by immunizing the mammal with said antigen is blended to the composition. In this case, the antiserum and milk as well as the antibody separated and purified from the antiserum and milk may be used. Each of these materials may be used alone or in a combination of two or more.

It is preferred that the amount of the above antibodies administered is 0.0001–50 g/kg/day and that the content of the above antibodies is 0.0002–10% by weight, preferably 0.002–5% by weight of the composition.

The oral composition of this invention which contains the above-mentioned serum or milk antibody may be prepared and used in various forms applicable to the mouth such as dentifrices including toothpastes, toothpowders and liquid dentifrices, liquid refrigerants including mouthwashes, solid refrigerants including troches and chewing gums, dental pastes, gingival massage creams, gargle tablets, dairy products including ice creams, yogurts and babaroa bases, and the like.

The oral composition according to this invention may further include additional well-known ingredients depending on the type and form of a particular oral composition. Any desired known ingredients may be mixed with said antibody.

In preparing dentifrice compositions, an abrasive may be blended generally in an amount of 5 to 95%, especially 15 to 60% by weight of the composition, including dicalcium phosphate dihydrate, dicalcium phosphate anhydrate, monocalcium phosphate, tricalcium tertiary phosphate, calcium carbonate, calcium pyrophosphate, silica abrasives, aluminum oxide, aluminum hydroxide, insoluble sodium metaphosphate, trimagnesium phosphate, magnesium carbonate, calcium sulfate, titanium dioxide, resins, and the like.

In preparing paste-like compositions, typically toothpastes, a binder may be blended generally in an amount of 0.3 to 5% by weight, including sodium carboxymethyl cellulose, methyl cellulose, sodium carboxymethyl hydroxyethyl cellulose, hydroxyethyl cellulose, sodium alginate, carrageenan, gum arabic, tragacanth gum, karaya gum, polyvinylalcohol, sodium polyacrylate, carboxyvinyl polymer, polyvinyl pyrrolidone, and the like.

In preparing paste-like and liquid oral compositions, typically toothpastes and mouthwashes, a humectant may be blended generally in an amount of 10 to 70% by weight, including polyethylene glycol, ethylene glycol, sorbitol, glycerol, propylene glycol, 1,3-butylene glycol, xylitol, maltitol, lactitol, and the like.

In addition to the above ingredients, a surface active agent including water soluble salts of alkyl sulfate having 8 to 18 carbon atoms such as sodium laurate and sodium myristate, sodium salts of higher fatty acids, water-soluble salts of sulfonates monoglycerides of higher fatty acids having 10 to 18 carbon atoms in the fatty acid group such as sodium lauryl monoglyceride sulfonate and sodium coconut monoglyceride sulfonate, sodium monoglyceride monosulfates of higher fatty acids, olefin sulfonates, paraffin sulfonates, sodium N-methyl-N-palmitoyl taurate, sodium N-lauroyl sarcosinate, sodium N-lauroyl-$\beta$-alaninate, stearyl monoglyceride, alkyrol ethanol amides such as lauroyl monoethanol amide and lauroyl diethanol amide, sucrose fatty acid esters having 12 to 18 carbon atoms in the fatty acid group such as sucrose monolaurate and dilaurate, lactose fatty acid esters, lactitol fatty acid esters, maltitol fatty acid esters, stearic acid monoglyceride, polyoxyethylene sorbitan monolaurate, polyoxyethylene-hardened castor oil, condensates of sorbitan monostearate with approximately 60 moles of ethylene glycol, condensates of ethylene oxide with propylene oxide, and their derivatives such as polyoxyethylene polyoxypropylene monolauryl ester, betaine and amino acid type amphoteric surfactants, and the like may be blended in an amount of 0 to 10%, preferably 0.1 to 5%, more preferably 1 to 2.5% by weight of the composition. A flavor such as an essential oil including peppermint oil and spearmint oil and a flavoring material including l-menthol, carvone, eugenol and anethole, a sweetener such as sodium saccharinate, stevioside, neohesperidyldihydrochalcone, glycyrrhizin, perillartine, p-methoxycinnamic aldehyde, a preservative, and the like may be blended in an effective amount.

In this invention, effective ingredients such as sorbic acid, alexidine, hinokitiol, cetylpyridinium chloride, alkyl glycine, alkyldiaminoethyl glycinate, allantoin, ϵ-aminocaproic acid, tranexamic acid, azulene, vitamin E, a water soluble primary or secondary phosphate, a quaternary ammonium compound, sodium chloride, enzymes such as dextranase, mutanase, lytic enzyme and protease, fluoride compounds such as sodium fluoride, stannous fluoride and sodium monofluorophosphate, chlorhexidine and its salts, bacteriocin, glucosyltransferase inhibitor, and crude drugs may also be blended in an effective amount.

Other types of compositions may also be prepared by selecting any desired ingredients as usual and mixing them by a conventional procedure.

Examples of the other ingredients for various types or forms of the composition are shown in the following examples.

Paste-like and liquid oral compositions may generally have a pH ranging from 5 to 10, but not limited thereto.

The oral composition of this invention, owing to blending the above-mentioned serum or milk autibody, can effectively prevent periodontal disease through the effective prevention of the colonization of *Bacteroides gingivalis* in the mouth.

In the following, examples of this invention will be given although this invention is not restricted them.

[EXAMPLE 1]

(1) Preparation of Antigens

After *Bacteroides gingivalis* 381 was cultured in Todd-Hewitt broth containing hemin and menadione for two days, the grown bacteria were collected through centrifugation carried out at 800 rpm for 15 minutes. The thus collected bacteria, after being washed with 5 mM phosphate buffer of pH 7.4, were treated in 0.5% formalin overnight, thereby obtaining the whole cell antigen.

As to the preparation of the pilus antigen, after *Bacteroides gingivalis* cultured for two days in the same manner as above was collected before being washed, the washed bacteria were gently stirred in distilled water containing glass beads for two days before being caused to pass through an No. 25 injection needle (0.5×25 mm) three times so as to sever the pili from the bacteria. The thus obtained solution was centrifuged at 8,000 rpm for 15 minutes to separate the bacteria from the pili contained in the supernatant, then the supernatant was dialyzed against distilled water before being lyophilized, thereby obtaining the pilus antigen. The yield was 0.0042% of the wet weight of the bacteria.

As to the capsule antigen, after bacteria collected in the same manner were allowed to react with phosphate buffer (0.05M, pH 7.4) containing 0.01M of EDTA at 60° C. for 30 minutes, the mixture solution was caused to pass through an No. 25 injection needle three times so as to separate the capsule from the bacteria. Next, the bacteria were removed by subjecting the thus obtained solution to centrifugation at 8,000 rpm for 15 minutes to obtain a supernatant which is then subjected to ultracentrifugation at 40,000 rpm for two hours, thereby obtaining a deposit which is used as the capsule antigen. The yield was 0.09% of the wet weight of the bacteria.

(2) Preparation of Antibodies

Serum antibodies were obtained by immunizing rabbits or pregnant sheep. Immunizations were carried out according to the usually adopted schedule. The initial immunization of rabbits with the whole cell antigen was carried out by subcutaneously injecting a mixture consisting of Freund's complete adjuvant and 20 mg of bacterial cells. Following the subcutaneous injection, 10 mg of bacterial cells was injected in the vein of the ear of the animal four times every seven days for a total of 40 mg. The antiserum obtained was subjected to salting-out in 50% ammonium sulfate solution two times before being dialyzed against distilled water, thereby obtaining an antibody preparation. Antibody preparations for the pilus antigen and the capsule antigen were obtained in the same manner as above.

Milk antibody was obtained by immunizing a goat of two month pregnancy with the whole bacterial cell antigen. The initial immunization of the pregnant goat was carried out by subcutaneously injecting a mixture consisting of Freund's complete adjuvant and 500 mg of bacterial cells, and other subcutaneous injections were carried out in the same manner 21 days and 28 days after the initial immunization. For the purpose of enhancing the production of the antibody contained in the milk, 500 mg of bacterial cells were orally administered 24 days after the initial administration. The milk was collected every day after the delivery. The collected milk was centrifuged at 15,000 rpm for one hour and the intermediate layer was collected. The thus collected layer was subjected to salting-out in 50% ammonium sulfate solution two times before being dialyzed against distilled water, thereby obtaining a goat's milk antibody preparation.

(3) Evaluation of the Antibodies

1. Reinforcing effects of rabbit's serum antibodies on the phagocytic ability of macrophages The reinforcing effects of the antibodies on the phagocytic ability against *Bacteroides gingivalis* were investigated by using guinea-pig's peritoneal macrophages.

Hanks' solution containing hemin and menadione was mixed with guinea-pig's perioneal macrophages obtained five days after the stimulation with oyster glycogen, *Bacteroides gingivalis* cultured for two days and each of various kinds of rabbit's antibodies (final concentration of 10%), and the mixture was subjected to anaerobic shake culture at 37° C. Then the number of living bacteria was measured 0, 0.5, 1, 2 and 3 hours after. In this experiment, $3.4 \times 10^5$ macrophages/ml were added and the survival rate observed three hours after was 95 to 97%. The results are shown in Table 1.

From the results shown in Table 1, the above various kinds of antibodies caused reinforcing effects to the phagocytic ability of macrophages as compared to the phosphate buffer (0.5M, pH 7.4) used as the control.

2. Effects of rabbit's serum antibodies inhibiting the colonization of *Bacteroides gingivalis* in Hamster's mouth

*Bacteroides gingivalis* cultured for three days were suspended in 1 mM phosphate buffer of pH 7.2 in such a manner that a suspension of 1.0 opacity ($OD_{550}=1.0$) was obtained. The thus obtained suspension was mixed with each of various kinds of antibodies in a ratio of 1 to 1, and the mixture was allowed to react at 37° C. for 30 minutes. In the control group, the suspension was caused to react with phosphate buffer in the same manner as above.

After the mandibular first molar of a golden hamster was ligated with a cotton thread (No. 50), 0.1 ml of the above obtained reaction solution was injected in the mouth and 0.1 ml of the same reaction solution was inoculated into the right and the left check poaches respectively. Inoculations with the above reaction solution were conducted for three consecutive days, and the ligation thread was removed one week after the last inoculation. Then the number of *Bacteroides gingivalis* and the number of anaerobic bacteria contained in the ligation thread were determined. During this experiment, in which nine animals were used for one group, the animals were given Diet 2000 of high sucrose content as feed and freely given tap water as drinking water. The results are shown in Table 2.

As clearly seen from the results given in Table 2, it was observed that the above various kinds of antibodies significantly inhibit the colonization of *Bacteroides gingivalis* in the mouth as compared to the control group.

3. Effect of goat's antibody inhibiting the colonization of *Bacteroides gingivalis* in the mouth The same method as above was adopted in carrying out an experiment. Goat's anti-whole cell milk antibody was used as a sample. The results are shown in Table 3.

As clearly seen from the results given in Table 3, it was observed that goat's milk antibody significantly inhibits the colonization of *Bacteroides gingivalis* in the mouth as compared to the control group.

TABLE 2

|  | Number of Animals in Which *B. gingivalis* was Detected | Number of *B. gingivalis*/ Number of anaerobic × 100 bacteria |
|---|---|---|
| Phosphate buffer (Control) | 9/9 | 4.06 ± 0.77 |
| Anti-whole cell antibody | 8/9 | 1.10 ± 0.41** |
| Anti-pili antibody | 9/9 | 1.03 ± 0.38** |
| Anti-capsule antibody | 9/9 | 0.79 ± 0.26** |

TABLE 1

|  | 0 hour | 0.5 hour | 1 hour | 2 hours | 3 hours |
|---|---|---|---|---|---|
| Phosphate buffer (Control) | $2.7 \times 10^5$ | $1.6 \times 10^5$ | $1.5 \times 10^5$ | $4.8 \times 10^5$ | $1.7 \times 10^4$ |
| Anti-whole cell antibody | $2.1 \times 10^5$ | $5.7 \times 10^4$ | $6.8 \times 10^3$ | $1.0 \times 10^3$ | $6.8 \times 10$ |
| Anti-pili antibody | $1.5 \times 10^5$ | $1.2 \times 10^4$ | $5.5 \times 10^3$ | $3.5 \times 10^3$ | $3.0 \times 10^2$ |
| Anti-capsule antibody | $2.4 \times 10^5$ | $8.4 \times 10^4$ | $1.8 \times 10^4$ | $1.1 \times 10^4$ | $1.5 \times 10^3$ |

TABLE 3

|  | Number of Animals in Which *B. gingivalis* was Detected | Number of *B. gingivalis*/ Number of anaerobic × 100 bacteria |
|---|---|---|
| Phosphate buffer (Control) | 8/9 | 0.50 ± 0.17 |
| Goat's anti-whole cell | 4/10 | 0.04 ± 0.03* |

TABLE 3-continued

| | Number of Animals in Which B. gingivalis was Detected | Number of B. gingivalis/ Number of anaerobic × 100 bacteria |
|---|---|---|
| milk antibody | | |

*P < 0.05

4. Effects of rabbit's serum antibodies inhibiting the colonization of *Bacteroides gingivalis* in Hamster's mouth by brushing

*Bacteroides gingivalis* cultured for three days was suspended in 1 mM phosphate buffer of pH 7.2 in such a manner that a suspension of 1.0 opacity ($OD_{550}=1.0$) was obtained. 0.1 ml of the thus obtained suspension was inoculated in the mouth of a golden hamster of which the right and left mandibular first molars were ligated with cotton threads (No. 50). Thirty minutes after the inoculation, 0.1 ml of the equivalent mixture of each kind of antibodies and glycerine and 0.1 ml of the equivalent mixture of water and glycerine were injected in the mouth respectively and buccal and lingual surfaces of the mandibular molars were brushed twenty times with a interdental brush. The above operations were conducted for three consecutive days, and thereafter only the brushing operation was conducted twice a day. One week and three weeks after the last inoculation, the ligation threads were removed. Then the number of *Bacteroides gingivalis* and the number of anaerobic bacteria contained in the ligation thread were determined. During this experiment, the animals were given Diet 2000 of high sucrose content as feed and freely given tap water as drinking water. The results are shown in Table 4.

As clearly seen from the results given in Table 4, it was observed that the above various kinds of antibodies significantly inhibit the colonization of *Bacteroides gingivalis* in the mouth as compared to the control group.

TABLE 4

| | One week later after inoculation | | Three weeks later after inoculation | |
|---|---|---|---|---|
| | Number of Animals in which B. gingivalis was Detected | Number of B. gingivalis/ Number of anaerobic × 100 bacteria | Number of Animals in which B. gingivalis was Detected | Number of B. gingivalis/ Number of anaerobic × 100 bacteria |
| Water (Control) | 8/8 | 0.305 ± 0.108 | 6/7 | 0.150 ± 0.047 |
| Anti-whole cell antibody | 6/8 | 0.051 ± 0.018 | 1/8 | 0.0004 |
| Anti-pili antibody | 4/8 | 0.052 ± 0.017 | 0/8 | 0 |
| Anti-capsule antibody | 6/8 | 0.031 ± 0.024 | 0/8 | 0 |

[EXAMPLE 2]

| Toothpste | |
|---|---|
| Dicalcium phosphate dihydrate | 50.0% |
| Glycerol | 20.0 |
| Sodium carboxymethyl cellulose | 1.0 |
| Sodium lauryl sulfate | 1.5 |
| Sodium lauroyl sarcosinate | 0.5 |
| Flavor | 1.0 |
| Sodium saccharin | 0.1 |
| Dextranase | 0.01 |
| Water | Balance |

| Toothpste | |
|---|---|
| | 100.0% |

The above components were blended with 0.1% or 0.2% of goat's anti-whole cell serum and 0.01% of chlorhexidine gluconate.

[EXAMPLE 3]

| Toothpaste | |
|---|---|
| Dicalcium phosphate dihydrate | 50.0% |
| Sorbitol | 10.0 |
| Glycerol | 10.0 |
| Sodium carboxymethyl cellulose | 1.0 |
| Sodium lauryl sulfate | 2.0 |
| Flavor | 1.0 |
| Sodium saccharin | 0.1 |
| Ethanol | 2.0 |
| Mutanase | 0.1 |
| Water | Balance |
| | 100.0% |

The above components were blended with 0.1% of bovine anti-capsule serum and 0.3% of sodium monofluorophosphate or 0.01% of chlorhexidine gluconate or 0.05% of lytic enzyme or 0.02% of bacteriocin.

[EXAMPLE 4]

| Toothpaste | |
|---|---|
| Calcium carbonate | 50.0% |
| Glycerol | 20.0 |
| Carrageenan | 0.5 |
| Sodium carboxymethyl cellulose | 1.0 |
| Lauroyl diethanolamide | 1.0 |
| Sucrose monolaurate | 2.0 |
| Flavor | 1.0 |
| Sodium saccharin | 0.1 |
| Water | Balance |
| | 100.0% |

The above components were blended with 0.05% of bovine anti-whole cell milk antibody, 0.005% of chlorhexidine gluconate and 0.05% of tranexamic acid.

[EXAMPLE 5]

| Toothpaste | |
|---|---|
| Dicalcium phosphate dihydrate | 50.0% |
| Glycerol | 20.0 |
| Sodium carboxymethyl cellulose | 2.0 |

-continued

| Toothpaste | |
|---|---|
| Sodium lauryl sulfate | 2.0 |
| Flavor | 1.0 |
| Sodium saccharin | 0.1 |
| Water | Balance |
| | 100.0% |

The above components were blended with 0.1% of equine anti-pilus serum and 0.01% of chlorhexidine gluconate or 0.05% of ε-aminocaproic acid.

[EXAMPLE 6]

| Toothpaste | |
|---|---|
| Silicic anhydride | 30.0% |
| Glycerol | 30.0 |
| Sorbitol | 20.0 |
| Sodium carboxymethyl cellulose | 1.0 |
| Sodium lauryl sulfate | 2.0% |
| Flavor | 1.0 |
| Sodium saccharin | 0.1 |
| Ethanol | 2.0 |
| Water | Balance |
| | 100.0% |

The above components were blended with 0.1% of sheep's anti-capsule serum and 0.1% of sodium fluoride or 0.01% of chlorhexidine gluconate or 0.1% of lytic enzyme or 0.01% of bacteroicin.

[EXAMPLE 7]

| Toothpowder | |
|---|---|
| Dicalcium phosphate dihydrate | 50.0% |
| Calcium carbonate | 30.0 |
| Glycerol | 10.0 |
| α-olefin sulfonate | 1.0 |
| Flavor | 1.0 |
| Sodium saccharin | 0.1 |
| Dextran | 0.5 |
| Water | Balance |
| | 100.0% |

The above components were blended with 0.1% of sheep's anti-pilus serum and 0.01% of chlorhexidine gluconate or 0.05% of lytic enzyme or 0.001% of bacteriocin.

[EXAMPLE 8]

| Liquid dentifrice | |
|---|---|
| Sodium polyacrylate | 50.0% |
| Glycerol | 30.0 |
| Flavor | 0.9 |
| Sodium saccharin | 0.1 |
| Ethanol | 3.0 |
| Linolic acid | 0.05 |
| Water | Balance |
| | 100.0% |

The above components were blended with 0.01% of goat's anti-whole cell milk antibody and 0.05% of chlorhexidine gluconate or 0.05% of lytic enzyme or 0.001% of bacteriocin.

[EXAMPLE 9]

| Mouthwash | |
|---|---|
| Ethanol | 20.0% |
| Flavor | 1.0 |
| Sodium saccharin | 0.05 |
| Lauroyl diethanol amide | 0.3 |
| Water | Balance |
| | 100.0% |

The above components were blended with 0.1% of goat's anti-capsule serum and 0.01% of chlorhexidine gluconate.

[EXAMPLE 10]

| Gargle tablet | |
|---|---|
| Sodium hydrogencarbonate | 54.0% |
| Disodium phosphate | 10.0 |
| Polyethylene glycol | 3.0 |
| Citric acid | 17.3 |
| Sodium sulfate (anhydrous) | 13.6 |
| Flavor | 2.0 |
| Oleic acid | 0.1 |
| | 100.0% |

The above components were blended with 0.1% of rabbit's anti-whole cell serum and 0.05% of chlorhexidine gluconate or 0.05% of lytic enzyme or 0.01% of bacteriocin.

[EXAMPLE 11]

| Gingival massage cream | |
|---|---|
| White petrolatum | 8.0% |
| Propylene glycol | 4.0 |
| Stearyl alcohol | 8.0 |
| Polyethylene Glycol 4000 | 25.0 |
| Polyethylene Glycol 400 | 37.0 |
| Sucrose monostearate | 0.5 |
| Water | Balance |
| | 100.0% |

The above components were blended with 0.5% of bovine anti-capsule serum and 0.01% of chlorhexidine gluconate or 0.1% of tocopheryl acetate.

[EXAMPLE 12]

| Chewing gum | |
|---|---|
| Gum base | 44.0% |
| Calcium carbonate | 2.0 |
| Starch syrup | 15.0 |
| Sugar | 30.0 |
| Sucrose palmitate | 1.0 |
| Fructose | 4.0 |
| Maltose | 3.0 |
| Flavor | 1.0 |
| | 100.0% |

The above components were blended with 0.1% of bovine anti-whole cell milk antibody and 0.01% of chlorhexidine gluconate or 0.1% of lytic enzyme or 0.01% of bacteriocin.

[EXAMPLE 13]

| Troche | |
|---|---|
| Gum arabic | 6.0% |
| Glucose | 72.0 |
| Gelatin | 3.0 |
| Flavor | 0.2 |
| l-menthol | 0.1 |
| Spearmint oil | 0.1 |
| Sodium ascorbate | 0.1 |
| Water | Balance |
| | 100.0% |

The above components were blended with 0.05% of goat's anti-pilus serum and 0.01% of chlorhexidine gluconate or 0.05% of lytic enzyme or 0.01% of bacteriocin or 0.05% of tocopheryl nicotinate.

[EXAMPLE 14]

| Dental paste | |
|---|---|
| Polyoxyethylene monostearate | 2.0% |
| Sorbitan monooleate | 2.0 |
| Cetyl alcohol | 2.0 |
| Palmityl alcohol | 3.0 |
| Propylene glycol | 15.0 |
| Sodium carboxymethyl cellulose | 5.0 |
| Gelatin | 1.0 |
| Sodium saccharin | 0.2 |
| Pepearmint oil | 0.5 |
| Spearmint oil | 0.5 |
| Lysozyme chloride | 5,000 units/g |
| Water | Balance |
| | 100.0% |

The above components were blended with 0.05% or 0.1% of equine anti-capsule serum and 0.1% of stannous fluoride or 0.01% of chlorhexidine hydrochloride or 0.05% of lytic enzyme or 0.01% of bacteriocin.

[EXAMPLE 15]

| Dental paste | |
|---|---|
| Glyceryl monolaurate | 3.0% |
| Oleyl alcohol | 5.0 |
| Polyethylene glycol | 15.0 |
| White petrolatum | 3.0% |
| N—palmitoyl monosodium glutamate | 0.5 |
| Hydroxyethyl cellulose | 5.0 |
| Tocopheryl acetate | 0.1 |
| Sodium saccharin | 0.2 |
| Japanese peppermint oil | 0.7 |
| Carvone | 0.5 |
| Anethole | 0.3 |
| Eugenol | 0.1 |
| Water | Balance |
| | 100.0% |

The above components were blended with 0.025% or 0.05% of rabbit's anti-pilus serum and 0.01% of chlorhexidine hydrochloride and 0.1% of β-glycyrrhiziric acid.

[EXAMPLE 16]

| Icecream | |
|---|---|
| Cream (fat content, 50%) | 16.84% |
| Milk (fat content, 3.7%)* | 42.65 |
| Defatted evaporated milk | 24.24 |
| Sugar | 11.25 |
| Corn syrup | 4.65 |
| Stabilizer | 0.35 |
| | 100.0% |

*Containing 0.5% of bovine anti-pilus mother's milk.

[EXAMPLE 17]

| Icecream | |
|---|---|
| Cream (fat content, 40%) | 31.54% |
| Milk (fat content, 3.7%)** | 37.16 |
| Defatted evaporated milk | 15.08 |
| Sugar | 11.25 |
| Corn syrup | 4.67 |
| Stabilizer | 0.30 |
| | 100.0% |

**Containing 5% of bovine anti-whole cell milk antibody.

[EXAMPLE 18]

| Yogurt | |
|---|---|
| Defatted milk | 320 kg |
| Evaporated milk containing sugar*** | 56 kg |
| Sugar | 23 kg |

The above components were fermented according to the usual method.
***Containing 10% of bovine anti-pilus mother's milk.

[EXAMPLE 19]

| Babaroa base | |
|---|---|
| Milk**** | 375 cc |
| Sugar | 60 g |
| Shell of vanilla | one |
| Yolk | five |
| Gelatin | 20 g |
| Fresh cream | 75 cc |

****Containing 5% of bovine anti-capsule mother's milk.

What is claimed is:

1. A dentifrice composition suitable for application to the mouth, comprising:
an effective amount to suppress the intraoral colonization of *Bacteroides gingivalis* of an antibody obtained by immunizing a mammalian animal with an immunologically effective amount of at least one antigen selected from the group consisting of *Bacteroides gingivalis*, a pilus fraction of *Bacteroides gingivalis* and a capsule fraction of *Bacteroides gingivalis*;
5 to 95% by weight of an abrasive; and
an orally acceptable carrier.

2. The composition of claim 1, wherein said antibody is present in an amount of 0.002 to 10% by weight of the composition.

3. The composition of claim 1, wherein said antibody is present in an amount of 0.002 to 5% by weight of the composition.

4. The composition of claim 1, which has a pH of from 5 to 10.

5. A method for treating periodontal disease in mammals caused by *Bacteroides gingivalis* which comprises applying to the mouth of a mammal an effective amount of the composition comprising:

an effective amount to suppress the intraoral colonization of *Bacteroides gingivalis* of an antibody obtained by immunizing a mammalian animal with an immunologically effective amount of at least one antigen selected from the group consisting of *Bacteroides gingivalis*, a pilus fraction of *Bacteroides gingivalis* and a capsule fraction of *Bacteroides gingivalis;* and an orally acceptable carrier to suppress the growth of *Bacteroides gingivalis*.

6. The method of claim 5, wherein the teeth of said mammal are brushed with said composition.

7. The method of claim 5, wherein said antibody in said composition is administered in an amount of 0.0001 to 50 g/kg/day based on the weight of said mammal.

8. The composition of claim 5, wherein said antigen is a whole cell antigen of *Bacteroides gingivalis*.

9. The composition of claim 1, wherein said antigen is the capsule fraction of *Bacteroides gingivalis*.

10. The composition of claim 1, wherein said antigen is the pilus fraction of *Bacteroides gingivalis*.

11. An oral composition suitable for application to the mouth, comprising:

an effective amount to suppress the intraoral colonization of *Bacteroides gingivalis* of an antibody obtained by immunizing a mammal selected from the group consisting of a rabbit, goat, sheet, horse and cow with at least one antigen selected from the group consisting of *Bacteroides gingivalis*, its pilus and capsule fractions wherein said effective amount is 0.0002 to 10% by weight of the composition;

5 to 95% by weight of the composition of an abrasive; and an orally acceptable carrier.

12. The composition of claim 11, wherein said antibody is separated and purified from antiserum or milk from a mammal which has been immunized with said antigen.

13. The composition of claim 11, wherein antiserum or milk obtained from a mammal which has been immunized with said antigen is added to the composition.

14. The composition of claim 11, wherein said antibody is present in an amount of 0.002 to 5% by weight of the composition.

15. The composition of claim 11, wherein said antibody is obtained by subcutaneously injecting said mammal with an antigen of *Bacteroides gingivalis*, thereafter intraveneously injecting said mammal with said antigen of *Bacteroides gingivalis*, collecting antiserum from the thus immunized mammal, salting-out the antibody from the antiserum and dialyzing said antibody to obtain a purified antibody.

16. A method for treating periodontal disease in mammals caused by *Bacteroides gingivalis* which comprises applying to the mouth of a mammal an effective amount of a composition comprising:

an effective amount to suppress the intraoral colonization of *Bacteroides gingivalis* of an antibody obtained by immunizing a mammal selected from the group consisting of a rabbit, goat, sheep, horse and cow with at least one antigen selected from the group consisting of *Bacteroides gingivalis*, its pilus and capsule fractions; and an orally acceptable carrier to suppress the growth of *Bacteroides gingivalis*.

17. The method of claim 16, wherein the teeth of said mammal are brushed with said composition.

18. The method of claim 16, wherein said antibody in said composition is administered in an amount of 0.0001 to 50 g/kg/day based on the weight of said mammal.

19. An oral composition suitable for application to the mouth, comprising:

an effective amount to suppress the intraoral colonization of *Bacteroides gingivalis* of a purified serum or milk antibody obtained by immunizing a mammalian animal with an immunologically effective amount of at least one antigen selected from the group consisting of *Bacteroides gingivalis*, a pilus fraction of *Bacteroides gingivalis* and a capsule fraction of *Bacteroides gingivalis;* and an orally acceptable carrier, said oral composition being in the form of a dentifrice, a liquid refrigerant, a solid refrigerant, a dental paste, a gingival massage cream, a gargle tablet or a dairy product.

20. The composition of claim 19, in the form of a dentifrice.

21. The composition of claim 19, in the form of a dental paste.

22. The composition of claim 19, in the form of a gingival massage cream.

23. The composition of claim 19, wherein said antibody is obtained by immunizing said mammal, collecting antiserum from said mammal, purifying said antibody in said serum and adding said purified antibody to said oral composition.

24. The composition of claim 19, wherein said antibody is obtained by immunizing said mammal with a pilus fraction of *Bacteroides gingivalis*.

25. The composition of claim 19, wherein said antibody is obtained by immunizing said mammal with a capsule fraction of *Bacteroides gingivalis*.

26. An oral composition suitable for application to the mouth, comprising:

an effective amount to suppress the intraoral colonization of *Bacteroides gingivalis* of an anti-pilus fraction of *Bacteroides gingivalis* antibody or an anti-capsule fraction of *Bacteroides gingivalis* antibody; and an orally acceptable carrier.

27. The composition of claim 26, wherein said antibody is an anti-pilus of *Bacteroides gingivalis* antibody.

28. The composition of claim 26, wherein said antibody is an anti-capsule fraction of *Bacteroides gingivalis* antibody.

29. The composition of claim 26, wherein said antibody is a serum antibody.

30. A method for treating periodontal disease in mammals caused by *Bacteroides gingivalis* which comprises applying to the mouth of a mammal an effective amount of the composition of claim 32.

31. The method of claim 30, wherein said composition is applied to the mouth by brushing buccal and lingual surfaces of molars.

* * * * *